United States Patent [19]

Weinheimer

[11] Patent Number: 5,225,447
[45] Date of Patent: Jul. 6, 1993

[54] COMPOSITION AND METHOD FOR THE TREATMENT OF SICKLE CELL ANEMIA

[75] Inventor: Alfred J. Weinheimer, Houston, Tex.

[73] Assignee: Omex International, Inc., Missouri City, Tex.

[21] Appl. No.: 835,404

[22] Filed: Feb. 14, 1992

Related U.S. Application Data

[60] Division of Ser. No. 529,459, May 29, 1990, Pat. No. 5,116,545, which is a continuation-in-part of Ser. No. 174,602, Mar. 28, 1988, abandoned, which is a continuation-in-part of Ser. No. 41,035, Apr. 22, 1987, abandoned.

[51] Int. Cl.$^5$ ............................................. A61K 31/20
[52] U.S. Cl. ..................... 514/815; 514/627; 514/560; 514/549; 514/552; 554/61; 554/213; 554/227; 424/195.1
[58] Field of Search ..................... 210/145; 424/195.1; 514/815; 554/224

[56] References Cited

U.S. PATENT DOCUMENTS 4,473,559  9/1984  Robinson ..................... 424/195.1

*Primary Examiner*—José G. Dees
*Assistant Examiner*—Deborah D. Carr
*Attorney, Agent, or Firm*—Waldron & Associates

[57] ABSTRACT

The major component of the carbonate fraction of free acids extractable from alfalfa has shown excellent control of symptoms in patients with sickle cell disease. Its structure has been established by proton NMR spectrometry as being 16-hydroxy-9Z,12Z,14E-octadecatrienoic acid and closely related compounds, such as simple esters, amides, triglycerides, or other derivatives of the carboxylic acid function, and a method for its synthesis from linseed oil or methyl linolenate has been developed. The product from linseed oil, both in the form of the initially formed triglyceride and in the form of its free acid obtained by saponification, is useful for the treatment of sickle cell disease.

8 Claims, No Drawings

COMPOSITION AND METHOD FOR THE TREATMENT OF SICKLE CELL ANEMIA

CROSS REFERENCE TO A RELATED APPLICATION

This is a division of application Ser. No. 07/529,459, filed May 29, 1990, now U.S. Pat. No. 5,116,545, which is a continuation-in-part application of copending application Ser. No. 174,602, of Sunday O. Fadulu and Alfred J. Weinheimer, filed on March 28, 1988, now which is in turn a continuation-in-part application of U.S. patent application Ser. No. 041,035, of Sunday 0. Fadulu and Alfred J. Weinheimer, filed on Apr. 22, 1987, now abandoned.

BACKGROUND OF THE INVENTION

The present invention relates to 16-hydroxy-9Z,12Z,14E-octadecatrienoic acid and closely related compounds, such as simple esters, amides, triglycerides, or other derivatives of the carboxylic acid function; isolated from the carbonate fraction of free acids extractable from various plant materials, particularly alfalfa. The invention also relates to compositions, containing the compounds, which are used for retarding red blood cell sickling associated with sickle cell disease.

Sickle cell disease is an inherited disease stemming from inadequate oxygen transport by an abnormal type of hemoglobin molecule in the red blood cells. It is an inherited disease which can be passed to offspring only if both parents carry the genetic trait. The trait carriers show no sign of the disease, but statistically one in four of their children will be afflicted with the disease. The disease is most prevalent in the black races, but is also known in other races surrounding the Mediterranean Sea and in India. It affects about 0.2% of the U.S. black population but is much more prevalent in central Africa.

The most common manifestation of the disease is an extremely painful "crisis," typically lasting several days, and affecting one or another local part of the body. The crisis often occurs following physical stress, and appears to be due to limited oxygen supply to the affected part. This is due to the inferior oxygen-carrying capability of the mutant hemoglobin, as well as to its tendency to aggregate in insoluble gels within the red blood cell, often leading to a form resembling a sickle. The distorted cells no longer freely traverse capillaries, further limiting oxygen supply to the tissues.

Despite the fact that the cause of sickle disease, i.e., the very minor structural variation in the mutant hemoglobin, has been known for many years, little progress has been made in suitable treatment of the disease. At the present time, the major treatment for the painful crises is medication for relief of pain, which merely treats the immediate symptom. Tissue damage, often involving major organs, occurs with each successive episode of oxygen deprivation, and the cumulative effects of the disease are debilitating and life shortening. Those afflicted with severe forms of the disease usually do not live through teen years.

Based on current knowledge of the disease, it appears feasible to develop a drug which will alleviate all of the symptoms of the disease and provide perfectly normal lives and life-expectancies for patients. This drug would not cure the disease, because it is genetic in origin, but if available, should effectively treat the disease by alleviation or prevention of its symptoms. The requisite capabilities of a potentially useful drug have been defined by the Sickle Cell Disease Branch of the U.S. National Institutes of Health (NIH). The requirements are specified in terms of several laboratory bioassays in which a candidate drug must perform successfully. No drug meeting these requirements has yet been announced. The drug of the present invention, however, displayed excellent responses in all the bioassays, as can be seen in the Examples below.

Fadulu (Fadulu, "Ethyl-Alcohol Extract From Fagara Zanthoxyloides Root: In vitro Effect on Red Blood Cells," Faculty Research Journal, Texas Southern University, 1:20–31 (1977)) reported in the 1970,s that the extract of the African chewing stick, prepared from the roots of the tree Fagara zanthoxyloides, possessed anti-sickling properties in in vitro studies.

Chemical studies were initiated to isolate and identify the active principle(s) in the extract responsible for this activity. Systematic fractionation of the extract, coupled with bioassay of the fractions produced at each stage, led to the isolation of a small amount of a mixture of rather polar compounds.

This mixture showed good activity in the blood-agar plate test developed by Fadulu to test for anti-sickling drugs. Sheep blood is dispersed in agar in a standard agar plate. On heating in a laboratory oven at 70° C. for 15 minutes, the red plates turn rust brown. If a drop of a solution of an effective anti-sickling drug is placed on the plate prior to heating, the blood under that spot remains red while the rest of the plate turns brown. The ready availability of this simple test sped the progress of the chemical work since fractions could be evaluated immediately by the chemical workers.

The chromatographic behavior of the components in the active fraction strongly suggested that they were acidic. Specifically, their TLC spots tailed badly, but were improved by the addition of a trace of acetic acid to the eluting solution. That they were indeed acids was confirmed by dissolving them in base, and then precipitating them with acid. Their presence as the free acids in the Fagara extract was confirmed in a similar experiment which resulted in their direct extraction, along with other acids, from the extract.

Because Fagara root was extremely difficult to obtain in adequate quantities, a quick survey of other plant materials was undertaken with the objective of locating a more readily available source. It was somewhat surprising to find that each of the new plant materials evaluated, primarily green vegetables, afforded the same TLC group of polar acids when extracted with dilute base. Additionally, each of the crude extracts showed good anti-sickling activity on red blood cells in vitro using the blood-agar plate test described above. Included were spinach, species *Spinacia oleracea*, mustard greens, species *Brassica juncea*, grass clippings, species *Stenotaphrum secundatum*, alfalfa, species *Medicagoo sativa*, and even fallen oak leaves, species *Quercus nigra*. The greatest quantities of acids were found in alfalfa, next greatest in hay, followed by Fagara, the reference point. Lesser quantities were present in grass clippings, still less in spinach and mustard greens, and least in oak leaves. Further, alfalfa, then hay, contained greater proportions of the most polar components. The less polar acids were common stearic, linolenic, linloleic, and oleic acids, which were of no interest. The alfalfa extract contained the novel compounds both in greater quantity and proportion; additionally, because alfalfa is commercially available year-round, alfalfa was selected for further study.

OBJECTS OF THE INVENTION

It is an object of the present invention to provide 16-hydroxy-9Z,12Z,14E-octadecatrienoic acid and closely related compounds, in the form of the free acids, and in their combined forms such as simple esters, amides, triglycerides, or other derivatives of the carboxylic acid function.

It is a further object to provide a method of making 16-hydroxy-9Z,12Z,14E-octadecatrienoic acid and closely related compounds, in the form of the free acids, and in their combined forms such as simple esters, amides triglycerides, or other derivatives of the carboxylic acid function from linseed oil or linolenic acid or its esters or other suitable derivatives.

It is another object of the present invention to provide a composition which is effective in the alleviation of the symptoms of sickle cell disease.

SUMMARY OF THE INVENTION

The mixture of free acids which is extractable from various plant materials has been shown to be useful in the treatment of sickle cell disease. It has been found that the mixture of acids can be separated into groups which are extractable from ethyl acetate solution by sodium bicarbonate, or by sodium carbonate, or by neither. The carbonate soluble fraction of acids showed the best in vitro antisickling activity, and was chosen for further study with the objective of isolating and identifying the active principle(s).

The major component in the mixture proved to be 16-hydroxy-9Z,12Z,14E-octadecatrienoic acid (Compound I). Compound I and other closely related compounds, such as its methyl ester and triglycerides containing Compound I, were synthesized from methyl linolenate and linseed oil.

Compound I and other closely related compounds, such as the methyl ester and triglycerides containing Compound I, were used in compositions which were found to be effective in the alleviation of the symptoms of sickle cell disease. The compounds may be mixed with appropriate pharmaceutically acceptable vehicles and administered orally, intravenously, subcutaneously, intraperitoneally, or via suppositories.

DETAILED DESCRIPTION OF THE INVENTION

Commercial alfalfa is available in a finely divided dried form in bags, and in the familiar field-dried bales. The former were used in bench studies, the latter in pilot scale work. The desired acid fraction was obtained by soaking the alfalfa in 3% aqueous sodium hydroxide for a minimum of 2 hours followed by filtration, acidification, and extraction of the free acids by hexane. In addition to sodium hydroxide, ammonium hydroxide and other alkali metal hydroxides such as potassium hydroxide may be used instead. Although hexane was the solvent of choice because it selectively dissolved the active acids, leaving other acidic material behind, its use was accompanied by severe emulsion problems. A useful alternative, particularly in large scale preparations, employed ?,1,1-trichloroethane (TCE) as the solvent for segregating the free acids following acidification of the extract. Other extraction solvents such as chloroform or methylene chloride may be used in place of TCE. Since considerable quantities of inactive acidic material were present in the TCE extract, the TCE soluble fraction was subsequently partitioned between hexane and methanol containing aqueous acid. The portion of the acids which thus partitioned into hexane were identical by thin layer chromatography (TLC) to the acid fraction obtained by direct extraction with hexane.

The brown-green mixture of acids produced in this fashion was referred to as the hexane fraction. It displayed good anti-sickling activity in the blood-agar plate test. Purification of the mixture was hindered by the presence of significant quantities of dark pigments which co-chromatographed with the desired acids in all systems evaluated.

It was found that the pigment could be overcome by partitioning an ethyl acetate solution of the hexane acids into three fractions which were 1) extractable by 5% sodium bicarbonate, 2) extractable by 5% sodium carbonate, and 3) extractable by neither. Most of the interfering pigments were found in the bicarbonate fraction, whereas the carbonate fraction was mostly pigment free. The yellow carbonate fraction was strongly active in the blood-agar plate test and by TLC showed a predominance of the characteristic spots always associated with active material. The bicarbonate fraction was less active, and showed the presence of some of the desired components, but the TLC pattern was strongly overlaid by a continuous streak of pigments. The fraction soluble in neither bicarbonate or carbonate was not significantly active.

Repeated reverse phase chromatography of the free acids in the carbonate fraction on $C_{18}$-silica gel was effective in removing the residual pigments, but failed to provide pure compounds as judged by TLC and proton magnetic-resonance (PMR) spectra. However, pure individual compounds were successfully obtained by chromatography of the mixture of methyl esters prepared by treating the enriched fractions of acids from the preceding chromatographies with diazomethane. In this manner, one major compound, and much smaller proportions of several closely related compounds were isolated in pure or nearly pure form, all as methyl esters of the naturally occurring acids. Their molecular weights were established by mass spectrometry and their structures were deduced by PMR spectroscopy. For the major compound, decoupling experiments clearly delineated all coupling patterns, and thus connectivities, in the molecule.

The major component in the mixture proved to be the methyl ester of 16-hydroxy-9Z,12Z,14E-octadecatrienoic acid (Compound II). Its molecular ion $M^+ = 308$, corresponded to the composition $C_{19}H_{32}O_3$. The PMR spectrum showed signals in the low field for a secondary alcohol and six olefinic protons. The high field region contained signals typical of an unsaturated fatty acid ester. The precise structure of Compound II was established by a series of decoupling experiments. In brief, the decoupling work showed first that the alcohol function was located at position 16, since its carbinyl hydrogen showed coupling to a methylene group (17) that in turn was coupled to the methyl group (18) at the end of the carbon chain. Proceeding next in the other direction along the chain, the carbonyl hydrogen was shown also to be coupled to a vinyl hydrogen (15) which in turn was coupled to another vinyl hydrogen (14), and that to another (13), and that to still another (12). This last vinyl hydrogen was coupled to a methylene group (11) which, from its chemical shift, was doubly allylic. This required that the remaining unsaturation be located between positions 10 and 9. The signals for H-9, although overlapped with those of H-10 and H-12, showed coupling to an allylic methylene (8).

The methylene (2) in the alpha position to the ester function was assignable from its chemical shift. This signal was shown to be coupled to another methylene (3) assignable to the β-position. The remaining atoms which were not accounted for in the decoupling experiments represented four methylene groups, which necessarily were situated between atoms 3 and 8, and which complete the structure assignment of Compound I.

The geometry of the double bonds in the conjugated diene system were assigned as 12-Z and 14-E (12-cis and 14-trans) on the basis of the magnitudes of their respective vicinal coupling constants. The coupling constants observed, $J_{12,13} = 10.8$ Hz and $J_{14,15} = 15.2$ Hz are typical of cis and trans double bonds, respectively.

The geometry of the non-conjugated double bond at position 9 could not be determined from the PMR spectrum since the coupling constant, $J_{9,10}$, could not be ascertained. The resonances for the H-9 and H-10 protons were overlapped with each other and with signal for H-12, and appeared as a non-first-order multiplet. However, as shown below, the geometry of this double bond was established as cis because of the identity of the ester prepared synthetically from all-cis methyl linolenate acid with that prepared from the extract.

No attempt was made to determine whether the natural acid or the derived methyl ester was optically active. Since the compound was obtained from natural sources and may be the result of enzymatic synthesis, it is possible that the compound occurs in nature as one of the two enantiomers due to optical activity at the single chiral center, position 16, in the molecule.

SYNTHESIS OF COMPOUNDS I AND II

As a synthetic objective, the structure of Compound I imposes some challenging and demanding requirements. These center not only on the regiochemical considerations for incorporation of the alcohol function and three olefinic centers in the proper positions within the eighteen carbon acid skeleton, but also on the more demanding geometric requirements for each of the double bonds.

Although it is possible to design synthetic approaches by which the detailed structure of Compound I could be constructed by sequential elaboration from simpler starting materials, any total synthetic approach would be both time-consuming and very expensive. The objective for a synthesis of Compound I, in addition to confirming the structure assigned by spectral methods, was to prepare Compound I by an inexpensive route, that would make the compound available for use as a therapeutic agent at a reasonable cost. From this practical standpoint, there would in fact be no need that the synthetic drug be of high purity. A product containing Compound I in even small amounts, ranging for example from about 0.001 to about 40% of the pharmaceutical composition, should serve quite adequately for clinical use as a therapeutic agent for sickle cell disease, much as the crude extract preparation, which contained possibly 5% of Compound I, has already shown efficacy in several small clinical trials.

The triply unsaturated $C_{18}$ fatty acid, linolenic acid, and its derivatives, such as methyl linolenate, were considered to be a potential starting material for synthesis of Compound I. It is present in large amounts in the form of triglycerides in certain vegetable oils. One of these, linseed oil, is a readily available and inexpensive article of commerce.

The synthesis of Compound I would involve isomerization of the 15,16-epoxide of linolenic acid to the allylic alcohol, as follows:

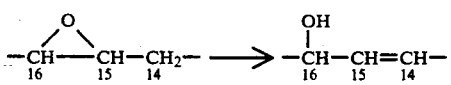

This type of transformation is normally effected by use of strong bases such as lithium diethylamide. Because the methylene group at position 14 is allylic to the 12,13-double bond in linolenic acid, its greater lability (compared to the alternate 17-methylene) would favor the desired regiochemical course of reaction.

The epoxidation was conducted using equimolar quantities of methyl linolenate and peracid which would be expected to form roughly equal amounts of the three possible epoxides and to avoid or minimize formation of bis-epoxides which could not lead to the desired product. See Example I. The epoxidation mixture, without any purification, was isomerized by heating with TsOH in benzene for several hours. See Example 2. Chromatography of the reaction mixture permitted isolation of a small amount of Compound II. Its PMR spectrum was identical to that of Compound II, which had been isolated previously as the major component of the mixture of methyl esters prepared from the acids of the carbonate fraction from the alfalfa extract, and its COSY spectrum fully substantiated the structure assigned earlier to Compound II on the basis of decoupling experiments. Also formed in this reaction was a mixture of the 1,2-diol monotosylates resulting from the well-known ring opening reaction of TsOH with epoxides.

In order to produce a large quantity of a form of Compound I for a clinical trial, the reaction sequence was applied next to linseed oil. The natural oil, known as raw linseed oil, is a triglyceride mixture in which approximately 50% of the combined acid is linolenic acid. Smaller quantities of linoleic (20%), oleic (20%), and saturated acids (10%) are also typically present. Epoxidation of raw linseed oil was performed with an equimolar amount of peracid, followed by TsOH catalyzed isomerization. See Examples 3 and 4. Following normal workup, but without further purification, the product of this reaction was used in a clinical trial. A portion of the triglyceride product was saponified to liberate the free acids which were also evaluated in that trial. See Example 5. A placebo consisting of raw linseed oil was included. Both the triglyceride and free acid forms of the drug were highly effective in eliminating crises and other adverse symptoms in sickle cell patients. No such effect was observed with the placebo. See Example 6.

EXAMPLE 1

Partial Epoxidation of Methyl Linolenate

A of 1.47 g (6.8 mmol) of m-chloroperoxybenzoic acid (80% purity) in 300 ml of methylene chloride was added over a period of three hours to a stirred solution of 5.0 g (17.1 mmol) of methyl linolenate in 250 ml of methylene chloride containing 1.4 g (16.6 mmol) of solid sodium bicarbonate. Stirring was continued for one hour after the addition was complete. A solution of 1.0 g (7.9 mmol) of sodium sulfite in 100 ml of water was then added with continued stirring for another 30 minutes. The aqueous layer was separated, washed three times with 50 ml of methylene chloride and the combined organic layers were washed twice with 50 ml of 5% sodium carbonate, twice with 50 ml of water, and then dried over anhydrous sodium sulfate. Removal of the solvent using a rotary evaporator at 40° C. and water aspirator vacuum afforded 4.5 g of pale yellow oil.

Chromatography of the partially epoxidized methyl linolenate on a silica gel column using a gradient of ethyl acetate in hexane for elution afforded unchanged methyl linolenate, its 12,13-epoxide, and an unseparated mixture of its 9,10- and 15,16-epoxides. These epoxides were characterized by proton NMR. In addition a small amount of slower moving material, probably the diepoxide and possibly triepoxide, was obtained but not characterized.

Example 2

Isomerization of Methyl Linolenate Epoxides by p-Tolunesulfonic Acid p-Toluenesulfonic acid (4.0 mg) was added a solution of 4.0 g of the crude epoxidation product prepared above in 250 ml of dry benzene. The mixture was heated at reflux for 4 hours. The benzene was removed at reduced pressure and the residue was taken up in 200 ml of ethyl acetate. The solution was washed with 50 ml of 5% sodium bicarbonate, 50 ml of water, and dried over sodium sulfate. Removal of the solvent under reduced pressure afforded a residue of 3.5 g of yellow oil. Chromatography on a silica gel column using a gradient of ethyl acetate in hexane for elution provided a pure sample of methyl 16-hydroxy-9Z,12Z,14E-octadecatrienoate. Its proton NMR spectrum was identical in all respects with that of the ester of the major component isolated from the carbonate fraction of the alfalfa extract.

EXAMPLE 3

Partial Epoxation of Linseed Oil

A solution of m-chloroperoxybenzoic acid (134.0 g, 0.62 mol) in 1 l of methylene chloride was added over a period of 2.5 hours to a stirred solution of 600 g (0.67 mol) of commercial raw linseed oil in 2 l of methylene chloride containing 60.0 g (0.71 mol) of sodium bicarbonate at room temperature. Stirring was continued for one hour after the addition was complete. A solution of sodium sulfite (50.0 g, 0.4 mol) in 1000 ml of water was then added, with continued stirring for another 30 minutes. The aqueous layer was separated and washed with 300 ml of methylene chloride. The combined organic layers were washed with three 1 l quantities of 5% sodium carbonate, 1 l of water, and dried over anhydrous sodium sulfate. Removal of the solvent under reduced pressure provided 550 g of a yellow oil.

EXAMPLE 4

Isomerization of Epoxidized Linseed Oil by p-Tolunesulfonic Acid p-Toluenesulfonic acid (4.5 g) was added to a solution of 300 g of epoxidized linseed oil in 1 l of dry benzene. The mixture was refluxed for 5 hours. A solution of 5 g of sodium bicarbonate in 100 ml of water was added, then the benzene was removed at reduced pressure. The oily residue was then dissolved in 1 l of ethyl acetate (to reduce emulsion problems), washed with 200 ml of water and dried over anhydrous sodium sulfate. Removal of the solvent under reduced pressure yielded 245 g of yellow oil. The triglyceride product, denoted Cpd. A, was evaluated in the clinical study whose results are reported below in Example 6.

EXAMPLE 5

Saponification of Isomerization Product

The above triglyceride (245 g, 0.27 mol) was dissolved in 850 ml of 95% ethanol. A solution of 56 g (1.0 mol) of potassium hydroxide in 150 ml of water was added and the mixture refluxed for 2 hours. The ethanol was removed at reduced pressure, 1 of water added, and the solution extracted once with 350 ml of ethyl acetate to remove neutral compounds. The aqueous solution was acidified with 6 N hydrochloric acid to pH 3 and extracted with three 250 ml portions of ethyl acetate. The combined organic phases were washed once with 250 ml of water and dried over anhydrous sodium sulfate. Removal of the solvent under reduced pressure yielded 204 g of pale yellow oil. The free acid form, denoted Cpd. B, was evaluated in the clinical study whose results are reported below in Example 6.

EXAMPLE 6

Clinical Study

The triglyceride product, denoted Cpd. A and described above in Example 4, the free acid form, denoted Cpd. B and described above in Example 5, and a placebo consisting of raw linseed oil, were administered in a clinical study to fifteen children, aged 6 to 15 years, over a period of 3 months. The fifteen patients used in this study were homozygous sickle cell patients who had had severe clinical courses. During the study the general condition of the children, their clinical symptoms, hematology, and biochemistry were observed.

At the beginning of the study, each patient was hospitalized for 10 days. A physical examination and laboratory tests were done to establish baseline activity levels of various body systems, including a complete blood count, liver function tests for serum bilirubin, alkaline phosphatase, transaminases, and serum protein, serum electrolytes, creatinine, BUN (blood urea nitrogen), and uric acid. On the second day, the patients started taking the drug and continued doing so for 10 days. Each patient was carefully monitored to check for possible side effects. At the end of the 10 days, the physical examination and laboratory tests were repeated and the patients discharged.

Drug administration continued on an out-patient basis and the patients were seen for evaluation once a week. At each visit, each patient was supplied with a week's course of the drug and was questioned about any subjective feeling which could indicate drug side effects, such as nausea, vomiting, diarrhea, and dizziness. The patient was also asked about the occurrence of crises or other problems. A physical examination was carried out and laboratory tests were run again. The trial lasted 3 months.

To facilitate administration, the compound was admixed with an inert medium, 100 mg of the compound in 75 mg of mineral oil in a gel capsule. The fifteen patients were divided into 3 groups of 5 (3 males and 2 females). The patients in group received gel capsules of Cpd. A in mineral oil. The patients in group 2 received gel capsules of Cpd. B in mineral oil. The patients in group 3 received gel capsules of raw linseed oil in mineral oil as a placebo. Each patient received 1 gel capsule a day, to ensure good serum levels.

The fifteen patients used in this study were homozygous sickle cell patients who had had severe clinical courses. They were all severely retarded in physical growth, and had all been hospitalized at least once. They all had stigmata of sickle cell anemia, that is skull bossing, gnathopathy, and hepatomegaly.

The only other medications taken by the patients during the study were the traditional folic acid and prophylactic anti-malarial medication.

Cpds. A and B and the placebo were tolerated well by the 15 patients. Not one patient complained of nausea, vomiting, dizziness, or diarrhea. A few comments were made concerning the taste of the medication.

At no time during the study was there any indication of bone marrow depression in the patients treated with Cpds. A and B. The hematocrit did not fall significantly in any of the patients at any time during the study. The total white blood cell count and differential counts did not show any adverse variation. The same applied to the platelet count.

There was no evidence, in the patients treated with Cpds. A and B, of hepato-toxicity, expressed, either as cholestasis or hepatocellular damage. In fact, there was a significant decrease in the combined mean value of the total serum bilirubin level before and after the trial. The conjugated bilirubin level and the serum alkaline phosphatase concentration also showed a sequential decrease in some of the patients.

Renal function was monitored by estimating the patients' serum creatinine and BUN levels serially. These parameters remained within normal limits, with no appreciable increase in their values in all the patients except for those in group 3. In fact when the BUN values for the patients treated with Cpds. A and B were considered together, there was a statistically significant decrease in the mean value at the end of the trial, in comparison to the initial value. The serum electrolytes and serum uric acid values remained normal, in the 10 patients in groups 1 and 2 throughout the duration of the study.

One of the established complications of sickle cell anemia is retardation of physical growth. The 10 patients in groups 1 and 2 of this study had marked stunting of physical growth. Each of them weighed below 55% of the expected weight for his/her age. In normal children and adolescents, the age of the patients in this study, the expected increase in weight per year is about 2.8 kg. This figure is, of course, much lower in sickle cell patients. It is, therefore noteworthy that each of the 10 patients gained considerable weight, ranging from 0.9 to 2.5 kg, in the 3 months, or less, that they were being treated with Cpds A or B. The mean weight at the end of the study was statistically higher than the initial value. Although anthropometric data were not always documented on routine clinical visits before the study, in the 10 patients for whom there was such documentation, none had shown this degree of weight gain before.

Hepatic enlargement is a common complication of sickle cell anemia and it has been documented in 30 to 50% of children with the disease. The cause of this, usually, is the blockage of the hepatic sinusoids by sickled erythrocytes, with consequent congestion.

The 15 patients in this study all had hepatomegaly, ranging from 5 to 13 cm (mean 6.9 cm) at the onset of the trial. Within 10 days of starting treatment with Cpds. A and B, there was noticeable reduction in all 10 patients in groups 1 and 2. By the end of the study, the liver was no longer palpable in one and was about 1 cm in another. The mean of the palpable liver size was 2.9 cm for the patients in groups 1 and 2, at the end of the study. The difference between this value and the initial one was highly significant.

This reduction in liver enlargement was the most striking uniform finding in these patients during this study. Three of the patients had had persistent enlargement of the liver for as long as they had been attending the sickle cell clinic before the study. It is, therefore, highly improbable that this uniform reduction in liver enlargement was a chance finding.

The other evidence for a beneficial effect of Cpds. A and B on hepatic function is the significant reduction in the mean value of the total serum bilirubin at the end of the trial. It is also noteworthy that the serum conjugated bilirubin fell sequentially in the 5 patients that had appreciably elevated values, at the beginning of the study. When these findings are considered along with the reduction in hepatic size, it could be inferred that Cpds. A and B reduced the degree of sinusoidal blockage (and obstructive jaundice) because of its antisickling properties.

The fact that Cpds. A and B possess anti-sickling properties is reflected by a reduction in the frequency of severe pain crises. All the patients in this study had frequent pain crises before they started taking the medication tested in this study. However, during the study, there was not a single episode of pain crisis that necessitated analgesic administration, in the patients who were treated with Cpds. A and B.

Cpds. A and B were shown in this study to be well accepted, non-toxic and may, indeed, be useful in the management of sickle cell disease. During this study, these drugs have demonstrated positive effects on body weight, hepatic function, and the frequency of severe pain crisis.

What is claimed is:

1. A method of treating sickle cell disease which comprises:
    combining an effective amount of an agent for treating sickle cell disease and a pharmaceutically acceptable carrier therefor, said agent comprising a compound which is a member of the group consisting of 16-hydroxy-9Z,12Z,14E-octadecatrienoic acid, simple esters of 16-hydroxy-9Z,12Z,14E-octadecatrienoic acid, simple amides of 16-hydroxy-9Z12Z,14E-octadecatrienoic acid, and triglyceride in which at least one of the combined acids in said triglyceride is 16-hydroxy-9Z,12Z,14E-octadecatrienoic acid; and
    administering said combined agent and vehicle.

2. The method of claim 1, wherein said combined agent and vehicle are administered by a technique selected from the group consisting of oral administration, intravenous administration, subcutaneous administration, intraperitoneal administration, and administration via suppositories.

3. A compound for the treatment of sickle cell disease which is a member of the group consisting of 16-hydroxy-9Z,12Z,14E-octadecatrienoic acid, simple esters of 16-hydroxy-9Z12Z,14E-octadecatrienoic acid, simple amides of 16-hydroxy-9Z,12Z,14E-octadecatrienoic acid, and triglyceride in which at least one of the combined acids making up said triglyceride is 16-hydroxy-9Z,12Z,14E-octadecatrienoic acid.

4. The compound of claim 3, wherein said compound is 16-hydroxy-9Z,12Z, 14E-octadecatrienoic acid.

5. The compound of claim 3 wherein said compound is the methyl ester of 16-hydroxy-9Z,12Z,14E-octadecatrienoic acid.

6. A pharmaceutical composition for the treatment of sickle cell disease which comprises:

an effective sickle cell disease treatment amount of a compound which is a member of the group consisting of 16-hydroxy-9Z,12Z,14E-octadecatrienoic acid, simple esters of 16-hydroxy-9Z,12Z,14E-octadecatrienoic acid, simple amides of 16-hydroxy-9Z,12Z,14E-octadecatrienoic acid, and triglyceride making up octadecatrienoic admixed with a pharmaceutically-acceptable vehicle.

7. The composition of claim 6, wherein said compound is 16-hydroxy-9Z,12Z,14E-octadecatrienoic acid.

8. The composition of claim 6, wehrein said compound is the methyl ester of 16-hydroxy-9Z,12Z,14E-octadecatrienoic acid.

* * * * *